United States Patent [19]
Ayra et al.

[11] Patent Number: 5,541,348
[45] Date of Patent: Jul. 30, 1996

[54] BILE ACIDS FOR BIOLOGICAL AND CHEMICAL APPLICATIONS AND PROCESSES FOR THE PRODUCTION THEREOF

[75] Inventors: Prabhat Ayra, Gatineau; Graham W. Burton, Orleans, both of Canada

[73] Assignee: National Research Council of Canada, Ottawa, Canada

[21] Appl. No.: 208,224

[22] Filed: Mar. 10, 1994

[51] Int. Cl.$^6$ .................. C07J 53/00; C07J 9/00
[52] U.S. Cl. .............. 552/506; 552/549; 552/542; 552/544; 552/551; 552/552; 552/553; 552/555; 552/540; 552/554; 540/109
[58] Field of Search .................. 552/506, 553, 552/549, 543; 540/109

[56] References Cited

U.S. PATENT DOCUMENTS 3,257,384  6/1966  Nelson et al. .................. 540/109
4,230,625  10/1980  Despreaux et al. .................. 552/551

OTHER PUBLICATIONS

CA108:34419, Riva et al, J. Org. Chem., 53(1), 88–92, 1988.
Kramer, W., J. Biol. Chem. 267:26: 18598–18604; 1992 Liver Specific Drug Targeting by Coupling to Bile Acids.
Zahalka, H. A. et al., J. Am. Chem. Soc. 113:7: 2797–2799; 1991 Bile Salt Modulated Stereoselection in the Cholesterol Esterase Catalyzed Hydrolysis of a–Tocopheryl Acetates.
Concepcion, J. I. et al. J. Org. Chem. 51:402–404 Iodosobenzene Diacetate, and Efficient Reagent for the Oxidative Decarboxylation of Carboxylic Acids, 1986.
Hernandez, R. et al., Synthesis 653–655, 1992 A Mild and Efficient Oxidation of Primary Athyl Iodides to Carboxylic Acids.
Kihira, K. et al., J. Lipid Res. 31:1323–1326, 1990 Synthesis of New Bile Salt Analogues, Sodium 3a, 7a–dihyroxy–5β–cholane–24–Sulfonate and Sodium 3a, 7β–dihydroxy–5β–Cholane–24–Sulfonate.

*Primary Examiner*—Rebecca Cook

[57] ABSTRACT

Novel bile acids according to the general formula

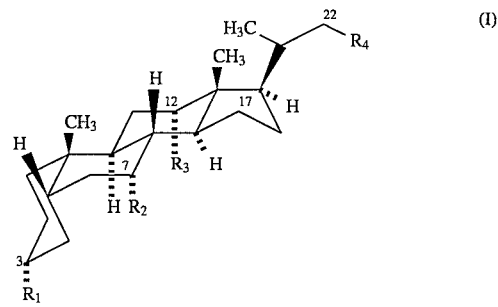

wherein $R_1$ represents a hydroxyl group, $R_2$ and $R_3$ both represent a hydrogen or a hydroxyl group, or $R_2$ represents a hydroxyl group or a β hydroxyl group and $R_3$ represents a hydrogen or $R_3$ represents a hydroxyl group and $R_2$ represents a hydrogen, and $R_4$ represents a $(CH_2)_nR_5$ wherein n is from 1 to 6, and $R_5$ represents $-O-PO(OH)_2$, $-CH(OH)COOH$, a nitrogen containing saturated heterocyclic ring group, $NR_6R_7$, wherein $R_6$ and $R_7$ are the same or different and each represent hydrogen or a $C_1$–$C_{10}$ alkyl group or $CO-R_8$ wherein $R_8$ represents an amino acid moiety, R-phenylglycine, 12-aminododecanoic acid or 4-aminohippuric acid are synthesized from cholic, deoxycholic, chenodeoxycholic, ursodeoxycholic and lithocholic acids and iodo-derivatives thereof by known processes and/or by novel processes according to the present invention. The novel processes of the present invention are (1) a free radical Michael-type chain lengthening approach and using a free radical mediator such as new tris(trimethylsilyl)silane (TTMSS); and (2) a malonate ester chain lengthening approach. The bile acids with systematic modifications in their structures can play an important role in understanding their mechanistic actions in biology and chemistry.

8 Claims, No Drawings

BILE ACIDS FOR BIOLOGICAL AND CHEMICAL APPLICATIONS AND PROCESSES FOR THE PRODUCTION THEREOF

FIELD OF THE INVENTION

The present invention relates to novel bile acids and to processes for the production thereof.

BACKGROUND OF THE INVENTION

Bile acids are synthesized in the liver from cholesterol and are essential to normal digestive and liver functions. The biological and chemical properties of bile acids have led to their use as therapeutic agents in the treatment of liver disease, cancer and for dissolving gallstones (Conference Proceedings *Bile Acids* 1993 *and the Future* California, USA, March 11–14,1993). For example, ursodeoxycholic acid has been shown to be an effective therapeutic agent in the treatment of primary biliary cirrhosis.

In biological systems, the amphiphilicity of bile salts assists in dissolving lipid-soluble substrates by facilitating contact with hydrolytic enzymes. For example, in the presence of bile salts, carboxylic ester hydrolase (cholesterol esterase) is known to hydrolyze water-insoluble esters, such as cholesterol, vitamin A, vitamin $D_3$ and vitamin E.

Recently, bile acids have been studied for their potential to deliver a drug molecule specifically into the liver and the biliary system (Kramer, W. et al, *J Bio Chem* 267: 26: 18598–18604; 1992). The studies suggest that hybrid molecules formed by covalent linkage of a drug to a bile salt are promising options for the delivery of liver-specific drugs and for enhanced intestinal absorption of drugs that are otherwise poorly absorbed.

Bile acids could also potentially play an important role in the treatment of cancer patients. One of the problems encountered during chemotherapy is that the efficacy of chemotherapeutic drugs is reduced because the drugs are rapidly metabolized in vivo by enzymes responsible for removing xenobiotics from cells in a living system. Bile acids, however, are known to interact with these enzymes. For example, glucuronosyl transferase is inhibited by lithocholic acid, thereby preventing the removal of xenobiotics from cells. However, lithocholic acid is highly toxic and, therefore, unsuitable for use in the treatment of cancer patients. It will be appreciated by those skilled in the art that a derivative of lithocholic acid with a similar ability for inhibiting the rate of metabolism of xenobiotics, for example chemotherapeutic drugs, while demonstrating a reduced toxicity could be very useful.

In another important development, the structure of bile salts was found to affect the stereoselectivity of cholesterol esterase in the hydrolysis of stereoisomers of vitamin E acetate, namely (2R,4'R,8'R)- and (2S,4'R,8'R)-α-tocopheryl acetates (RRR-and SRR-α-TAc, respectively) (Zahalka, H. A. et al *J Am Chem Soc* 113: 7: 2797–2799; 1991). In the presence of cholic acid as the obligatory bile salt, the rate of hydrolysis of SRR-α-TAc was greater than that of the RRR-stereoisomer. However, when the obligatory bile salt was changed to glycocholate and to taurocholate, the rate of hydrolysis of the RRR-α-TAc was higher under similar reaction conditions, thereby indicating modulation of chiral recognition by changing the bile salt. These studies strongly suggest that chiral bile salts act, in this case, as a stereomodulator of enzymatic hydrolysis, rather than acting to solubilize the substrate. Modulation of chiral recognition is especially noteworthy in this example because the chiral center is separated by six bonds from the hydrolysis site.

One of the major problems in understanding the mechanisms of actions of bile acids is the lack of availability of a wide variety of bile acids with systematic modifications in their structures. It is believed that new bile acids with systematic modifications in their structures can play an important role in understanding their mechanistic actions in biological and chemical applications.

It is an object of the present invention to synthesize novel bile acids that are derived from cholic, deoxycholic, ursodeoxycholic and lithocholic acids. It is another object of the present invention to provide novel bile acids with systematic modifications in their structures for use in studying the mechanistic actions of the novel bile acids; in biological and chemical applications, including interaction with enzymes, effectiveness in the treatment of cancer and other diseases and as an agent for dissolving gallstones.

SUMMARY OF THE INVENTION

According to one aspect of the present invention, there is provided a bile acid according to the general formula (I)

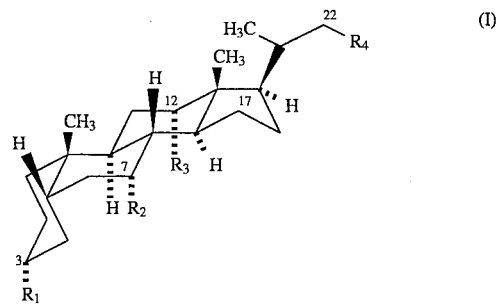

wherein $R_1$ represents a hydroxyl group, $R_2$ and $R_3$ both represent a hydroxyl group, or $R_2$ represents a hydroxyl group or a β-hydroxyl group and $R_3$ represents hydrogen, and $R_4$ represents —$(CD_2)_n R_5$ wherein n is from 1 to 6, and $R_5$ represents (i) —$CH(COOH)_2$, —O—$PO(OH)_2$, or —CH(OH)COOH, or (ii) —CO—$R_6$ or —CO—$NHC_6H_4$—$NHCH_2COOH$, wherein $R_8$ represents an amino acid moiety.

According to another aspect of the present invention, there is provided a process for the production of a bile acid according to the general formula (I)

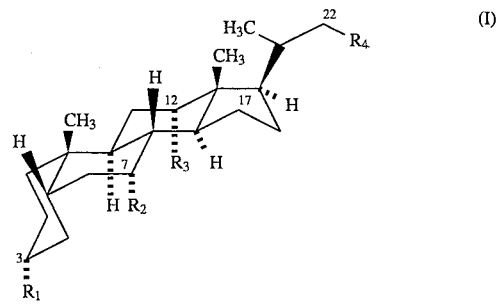

wherein R1 represents a hydroxyl group, R2 and $R_3$ both represent a hydrogen or a hydroxyl group, or R2 represents a hydroxyl group or a β hydroxyl group and $R_3$ represents a hydrogen or $R_3$ represents a hydroxyl group and $R_2$ represents a hydrogen, and $R_4$ represents a —COOH group or $(CH_2)_n COOH$ wherein n is 3 to 6, comprising, in a first step, reacting a bromo- or iodo-derivative according to the general formula (III)

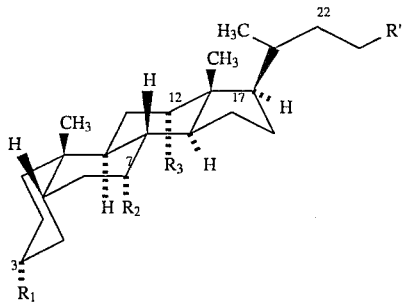

(III)

wherein $R_1$, $R_2$ and $R_3$ have the above-mentioned meanings and R' represents $(CH_2)_kI$ or $(CH_2)_kBr$ wherein k is from 0 to 3, with alkyl acrylate and tris(trimethylsilyl)silane in the presence of a free radical initiator to produce an intermediate compound according to the general formula (IV)

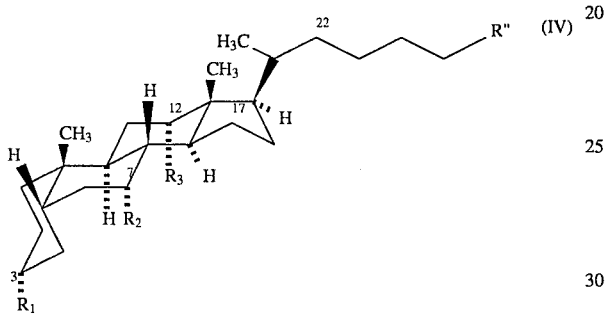

(IV)

wherein $R_1$, $R_2$ and $R_3$ have the above-mentioned meanings and R" represents $(CH_2)_kCOOEt$ and k is from 0 to 3, and, in a second step, reacting the intermediate compound (IV) to hydrolyze the ester to an acid of the general formula (I).

According to a further aspect of the present invention, there is provided a process for the production of a bile acid according to the general formula (I)

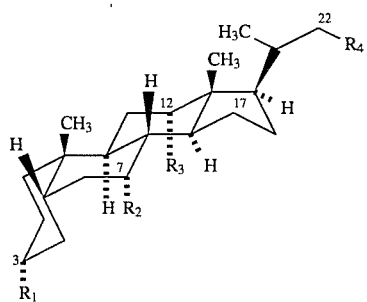

(I)

wherein $R_1$ represents a hydroxyl group, $R_2$ and $R_3$ both represent a hydrogen or a hydroxyl group, or $R_2$ represents a hydroxyl group or a β hydroxyl group and $R_3$ represents a hydrogen or $R_3$ represents a hydroxyl group and $R_2$ represents a hydrogen, and $R_4$ represents $(CH_2)_zCOOH$ or $(CCH_2)_{z-1}CH(COOH)_2$, wherein z is from 2 to 6, comprising, in a first step, reacting a bromo- or iodo-oderivative according to the general formula (III)

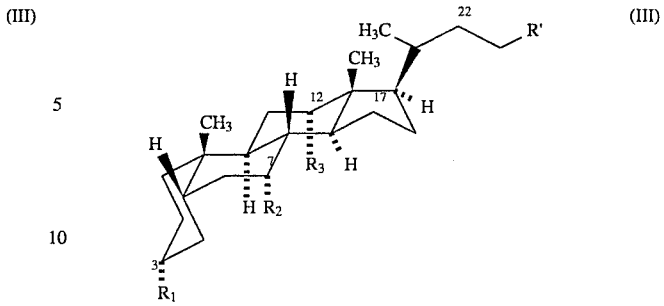

(III)

wherein $R_1$, $R_2$ and $R_3$ have the above-mentioned meanings and R' represents $(CH_2)_xI$ or $(CH_2)_xBr$, wherein x is from 0 to 4, with a malonate ester under aprotic conditions, for instance in the presence of a metal hydride base preferably in the presence of a sodium hydride to produce an intermediate, and in a second step, reacting the intermediate to hydrolyze the ester of an acid of the general formula (I).

DETAILED DESCRIPTION OF THE PREFERRED EMBODIMENTS

The novel bile adds of the present invention are synthesized from known bile acids such as cholic, deoxycholic, chenodeoxycholic, ursodeoxycholic and lithocholic adds of the general formula (II)

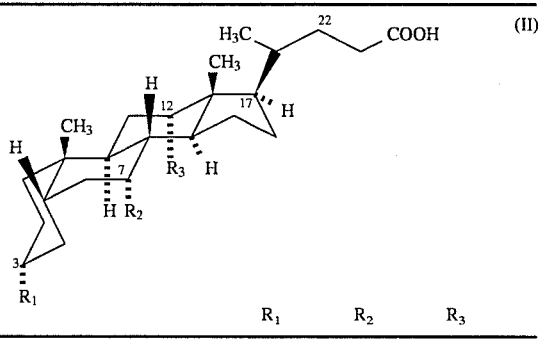

(II)

|  | $R_1$ | $R_2$ | $R_3$ |
|---|---|---|---|
| Cholic acid | OH | OH | OH |
| Deoxycholic acid | OH | H | OH |
| Chenodeoxycholic acid | OH | OH | H |
| Ursodeoxycholic acid | OH | βOH | H |
| Lithocholic acid | OH | H | H | wherein $R_1$ represents a hydroxyl group, $R_2$ and $R_3$ both represent a hydrogen or a hydroxyl group, or $R_2$ represents a hydroxyl group or a β hydroxyl group and $R_3$ represents a hydrogen or $R_3$ represents a hydroxyl group and $R_2$ represents a hydrogen. When $R_1$, $R_2$ and $R_3$ each represent a hydroxyl group, the bile acid of the general formula (II) is cholic acid. When $R_1$ and $R_3$ both represent a hydroxyl group and $R_3$ represents hydrogen, the bile acid of the general formula (II) is deoxycholic acid. When $R_1$ and $R_2$ both represent a hydroxyl group and $R_3$ represents hydrogen, the bile acid of the general formula (II) is chenodeoxycholic acid. When $R_1$ represents a hydroxyl group, $R_2$ represents a β-hydroxyl group and $R_3$ represents hydrogen, the bile acid of the general formula (II) is ursodeoxycholic acid. When $R_1$ represents a hydroxyl group, and $R_2$ and $R_3$ both represent hydrogen, the bile acid of the general formula (II) is lithocholic acid.

In accordance with the present invention, the bile acids according to the general formula (II) are modified in the side chain to produce novel bile acids according to the general formula (I)

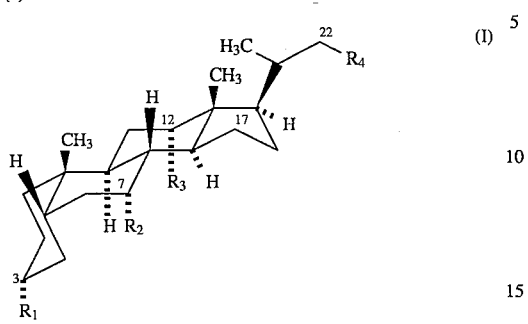

wherein $R_1$ $R_2$ and $R_3$ have the same meanings as for the general formula (II), and $R_4$ represents a carboxy group or $(CH_2)_n R_5$ wherein n is from 1 to 6, and R5 represents —COOH, —(COOH)$_2$, —O—PO(OH)$_2$, —CH(OH)COOH, a nitrogen containing saturated heterocyclic ring group, $NR_6 R_7$, wherein $R_6$ and $R_7$ are the same or different and each represent hydrogen or a $C_1$–$C_{10}$ alkyl group or CO—$R_8$ wherein $R_8$ represents an amino acid moiety, R-phenylglycine, 12-aminododecanoic acid or 4-aminohippuric acid, In particular, the novel bile adds of the present invention are:

nor-derivatives, such as,

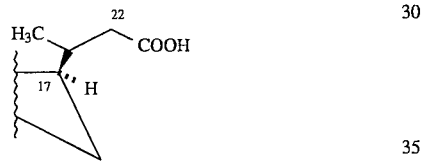

homo-derivatives, such as,

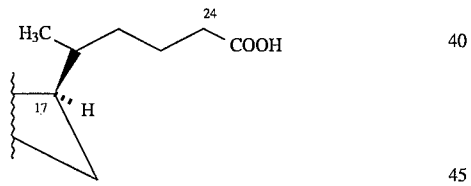

bishomo-derivatives, such as,

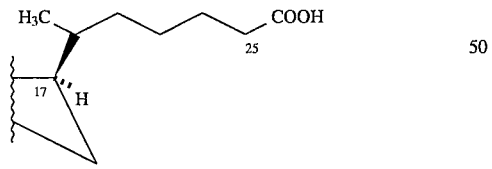

trishomo-derivatives, such as,

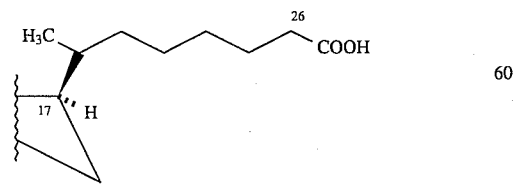

α-carboxy-homo- and α-carboxy-bishomo-derivatives, such as,

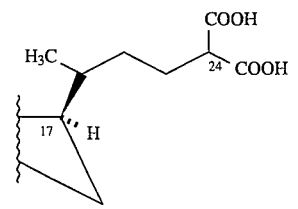

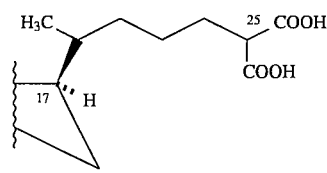

phosphate derivatives, such as

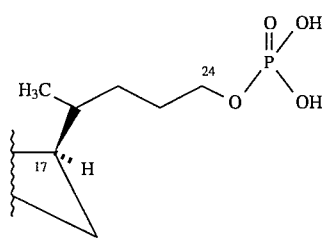

α-hydroxyl-derivatives, such as,

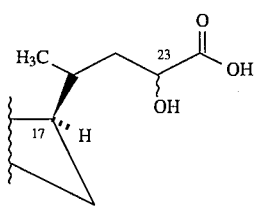

nitrogen containing side chain derivatives, such as,

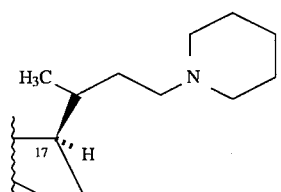

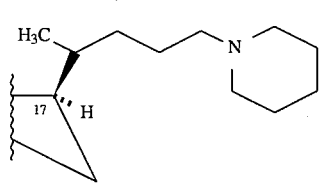

and L-aspartate, L-glutamate, L-lysine,

R-phenylglycine, 12-aminododecanoic acid and 4-aminohippuric acid conjugate derivatives, such as,

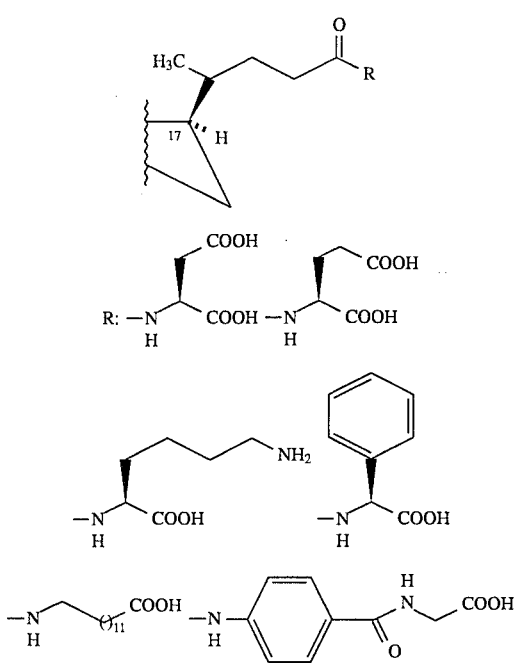

of cholic, deoxycholic, chenodeoxycholic, ursodeoxycholic and lithocholic acids.

The novel bile acids are synthesized by known and/or novel processes according to the present invention. The modifications used to produce these novel bile acids are classified below and each will be described in more detail hereinafter. In summary, in accordance with the present invention, cholic, deoxycholic, chenodexoycholic, ursodeoxycholic and lithocholic acids are modified by:

(a) variation in the length of the side chain between the carboxy group and the steroidal skeleton of the bile acid;

(b) addition of another carboxy group at the α-position on the side chain of the bile acid;

(c) incorporation of a phosphate group on the side chain of the bile acid;

(d) incorporation of a hydroxyl group at the α-position on the side chain of the bile acid;

(e) incorporation of a positively charged group such as piperidine hydrochloride on the side chain of the bile acid; and/or (f) conjugates of amino acid derivatives such as L-aspartate, L-glutamate, L-lysine, R-phenylglycine, 12-aminododecanoate and 4-aminohippuric acid.

The novel processes of the present invention are (1) a free radical chain lengthening Michael-type approach using a free radical mediator such as tris(trimethylsilyl)silane (TTMSS); and (2) a malonate ester chain lengthening approach. These two approaches are used to increase the length of the side chain between the carboxy group and the steroidal skeleton of the bile acid and to incorporate an additional functional group, such as a carboxy group in the side chain, starting from an iodo-derivative of a bile acid.

The nor-derivative is prepared by converting a bile add according to the general formula (II) into an iodo-derivative of the general formula (III) by a known procedure, for example as described in Concepcion, J.I. et al *J Org Chem* 51: 402–404; 1986. The side chain of the iodo-derivative is then shortened by one carbon unit according to a known method, for example as described in Hernandez, R. et al *Synthesis* 653–655; 1992. Examples of the novel bile acids of the present invention are 23-nor-cholic, chenodeoxycholic and ursodeoxycholic acids.

The homo- and α-carboxy-homo derivatives of a bile acid according to the general formula (II) are synthesized by reacting an iodo-defivative, prepared as above, with dimethyl- or diethyl-malonate according to the malonate ester chain lengthening approach of the present invention. The resulting product, homo- or α-carboxy-homo derivative, is dependent on the temperature of reaction. The homo-derivative is prepared by lengthening the side chain of the bile acid by one carbon unit, while the α-carboxy-homo derivative is prepared by incorporating an additional α-carboxy group on the side chain of the bile acid according to the general formula (II). Examples of the bile acids of the present invention are 25-homo- and 24-carboxy-25-homocholic, deoxycholic, chenodeoxycholic, ursodeoxycholic and lithocholic acids prepared from an iodo-defivative of the corresponding bile add according to the general formula (III), wherein R' represents iodine. When the starting material is an iodo-derivative of the general formula (III) wherein R' represents $CH_2I$, the novel bile acids produced are 25-carboxy-26-bishomocholic, deoxycholic, chenodeoxycholic, ursodeoxycholic and lithocholic acids.

The bishomo- and trishomo-defivative are prepared according to the free radical approach of the present invention by generating a carbon-centered radical of an iodo-defivative prepared as above and trapping the radical with methyl or ethyl acrylate. Examples of the novel bile adds of the present invention are 26-bishomo- and 27-trishomocholic, deoxycholic, chenodeoxycholic, ursodeoxycholic and lithocholic acids.

The phosphate-derivative is prepared from a bile acid according to the general formula (II) by phosphorylation of the hydroxyl group according to a method known to those skilled in the art. Examples of the novel bile adds of the present invention are 24-O-(phosphate)-cholan tetrol, deoxycholan triol, chenodeoxycholan triol, ursodeoxycholan triol and lithocholan diol.

The α-hydroxyl derivative is prepared by hydroxylation of a bile acid according to the general formula (II) using Davis reagent according to a method known to those skilled in the art. Examples of the novel bile adds of the present invention are 23-hydroxy-cholic, deoxycholic, chenodeoxycholic, ursodeoxycholic and lithocholic acids.

The nitrogen containing side chain derivatives are prepared by incorporating a positively charged group, such as piperidine hydrochloride, in an iodo-derivative as prepared above, according to a method known to those skilled in the art. Examples of the novel bile acids of the present invention are 23-N-piperidino- and 24-N-piperidino-cholane, deoxycholane, chenodeoxycholane, ursodeoxycholane and lithocholane.

The L-aspartate, L-glutmate, L-lysine, R-phenylglycine, 12-aminododecanoic acid and 4-aminohippuric acid conjugate derivatives were prepared by a dicyclohexylcarbodiimide (DCC) activation method known to those skilled in the art. Examples of the novel bile adds of the present invention are L-aspartate, L-glutamate, L-lysine, R-phenylglycine, 12-aminododecanoic acid, and 4-aminohippuric acid conjugates of cholic, deoxycholic, chenodeoxycholic, ursodeoxycholic and lithocholic acids.

A number of novel derivatives of lithocholic acid were synthesized to test their ability to inhibit glucuronosyl transferase activity in colon cells. It was discovered that nor-lithocholic acid and bishomo-lithocholic acid had inhibition properties very similar to lithocholic acid. It is anticipated that norlithocholic acid and bishomo-lithocholic acid could, therefore, be useful in colon cancer therapy studies.

The modification of cholic acid to α-carboxy-homocholic acid derivative has been found to modulate chiral recognition during the enzymatic hydrolysis of SRR- and RRR-α-TAc. For example, with cholic acid the ratio of the products was 3:1 (SRR-:RRR—OH). The ratio was changed to 1:8 when cholic acid was replaced by α-carboxy-homocholic acid. Modulation in chiral recognition was also observed when bishomo-cholic acid or trishomo-cholic acid was used to replace cholic acid.

Earlier studies have shown the dihydrobenzofuran (DHBF) analog of vitamin E to be a better antioxidant than vitamin E acetate (Burton, G. W. and Ingold, K. U. *Acc Chem Res* 19: 194–201; 1986). In the past, most of the experiments were carried out with a racemic sample of the DHBF analog because of the difficulty in obtaining a pure sample of the RRR-stereoisomer. Enzymatic hydrolysis of the racemic-DHBF analog of vitamin E (racetalc at C-2, SRR-and RRR-stereoisomers) in the presence of cholic acid gave phenolic products in a ratio of 5:1 (SRR- :RRR—OH). This ratio was changed to 1:16 (SRR- :RRR—OH) when cholic acid was replaced by α-carboxy-homo-cholic acid.

The following Examples illustrate the present invention. All of the reactions were conducted in an $N_2$ atmosphere.

EXAMPLE 1

Synthesis of nor-derivatives by shortening side chain by one carbon unit 50.0 mmol of a commercially available 5β-cholanic acid-3α,7α,12α-atriol (Sigma Chemical Company, St. Louis, Mo., U.S.A.) was added to a 500 ml flask under $N_2$ with 20 ml pyridine, 100 ml acetic anhydride, 10 mol % 4-dimethylaminopyridine (DMAP) as a catalyst and 300 ml $CH_2Cl_2$. The mixture was stirred at room temperature overnight. The resultant mixture was washed with a saturated solution of $NH_4Cl$. The organic layer was collected and dried over $MgSO_4$. Evaporation of the organic solvent yielded 90–95% of a tri-O-acetyl-derivative of cholic acid as a white solid. Results of analysis of the tri-O-acetyl-derivative were: LC-MS (thermospray):535 $(M+H)^+$, 552$(M+NH_4)^+$.

An iodo-derivative according to the general formula (III), wherein $R_1$, $R_2$, and $R_3$ each represent a hydroxyl group and R' represents iodine, was prepared from the tri-O-acetyl-derivative by a method reported in the literature (Concepcion, J. I. et al *J Org Chem* 51: 402–404; 1986) as follows. A solution of the tri-O-acetyl-derivative (1 mmol) in carbon tetrachloride (75 ml) containing iodosobenzene diacetate (IBDA, 0.55 mmol) and iodine (0.5 mmol) was irradiated with two 100-W tungsten-filament lamps for 45 minutes at reflux temperature. Additional portions of IBDA (0.55 mmol) and iodine (0.5 mmol) were added and irradiation was continued at this temperature for 45 minutes. The mixture was washed with diluted sodium thiosulfate and water. The iododerivative was purified over silica gel. Results of analysis of the iodo-derivative were: LC-MS (thermospray): 617 $(M+H)^+$, 635 $(M+NH_4)^+$; $^{13}$C-NMR: 170.4, 170.3, 77.0, 75.3, 74.0, 70.6, 47.3, 45.1, 43.3, 40.9, 40.0, 37.7, 36.4, 34.7, 34.3, 31.2, 28.8, 27.2, 26.8, 25.5, 22.7, 22.5, 21.6, 21.4, 17.0, 12.2 and 4.59.

The iodo derivative (4.0 mmol) was added to a round-bottom flask equipped with a Teflon-coated magnetic stirring bar, containing $CCl_4$ (50 mL), acetonitrile (50 ml), water (80 ml) and periodic acid (3.73 g, 16.4 mmol). The mixture was stirred at room temperature for 20 minutes and ruthenium (III) chloride hydrate (0.033 g, 0.16 mmol) was added. The mixture further stirred at room temperature for 24 h. The reaction flask was cooled to 0° C. with an ice bath, and ether (45 ml) was added. The organic layer was dried over $MgSO_4$, filtered, and the solvent evaporated. The crude residue was dissolved in ethanol (200 ml) and p-toluenesulphonic acid (0.76 g, 4.0 mmol) was added. The solution was refluxed at 90° C. overnight. The solvent was evaporated, the residue dissolved in methylene chloride, and usual work up was performed. The solvent was evaporated and the intermediate was purified by chromatography. (Hernandez, R. et al *Synthesis* 653–655; 1992).

Results of analysis of the intermediate were: LC-MS (thermospray): 566 $(M+NH_4)^+$, 580 $(M+CH_3OH)^+$; $^{13}$C-NMR: 173.4, 170.7, 170.6, 75.4, 74.3, 70.9, 60.4, 47.6, 45.3, 43.6, 41.6, 41.1, 37.9, 34.8, 34.5, 33.3, 31.5, 29.1, 27.5, 27.1, 25.8, 23.0, 22.8, 21.8, 21.7, 18.9, 14.5 and 12.4.

The intermediate was dissolved in 50 ml ethanol and 10 ml 1N sodium hydroxide was added thereto. The mixture was refluxed overnight and acidified with dilute hydrochloric acid. The product precipitated out and was filtered to give 23-nor-5β-cholanic acid-3α,7α,12α-triol as a white solid (93–95%). Results of analysis of the product, 23-nor-5β-cholanic acid-3α,7α,12α-triol, were: LC-MS (thermospray): 426 $(M+H+CH_3CN)^+$.

The nor-derivatives of deoxycholic, chenodeoxycholic, ursodeoxycholic and lithocholic acids were prepared in the same manner with similar results.

The reaction scheme of Example 1 is presented below.

Side Chain Shortening by One Carbon Unit

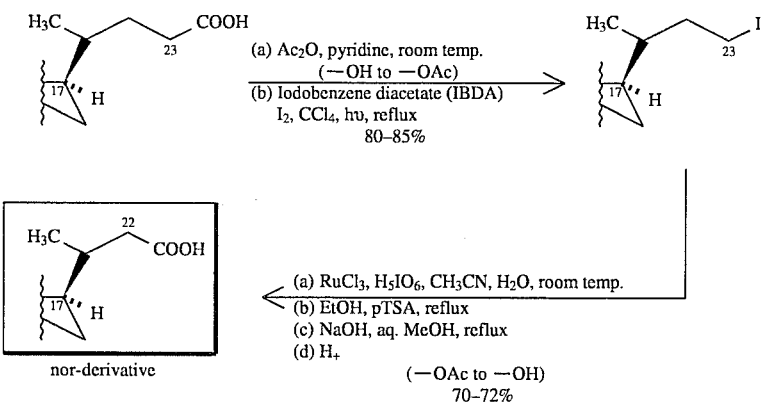

EXAMPLE 2

Synthesis of homo- and α-homo-carboxy derivatives by lengthening side chain by one carbon unit and by incorporating αcarboxy group NaH (0.54 g, 22 mmol) was added to a solution of diethylmalonate (1.6 ml, 10 mmol) in 150 ml tetrahydrofuran (THF) and stirred at 40° C. for 20 minutes. Then, a solution of an iodo-derivative (10 mmol) prepared as described in Example 1 and dissolved in 20 ml THF was added dropwise thereto. The mixture was warmed at 40° C. for 3.5 hours. The reaction was diluted by 300 ml $CH_2Cl_2$ and the organic layer was washed with 50 ml pH 7 buffer solution. The organic layer was collected, dried and evaporated to dryness. The residue was purified over silica gel (solvent system: ethyl acetate/hexane, 1:3) to give 25–28% of the starting material (iodo-derivative) and 24-carboxy-25-homo-5β-cholanic acid-3α,7α,12α-triacetoxy-ethyl ester as a white solid (60–67%; 80–86% based on the recovered starting material). Results of analysis of 24-carboxy-25-homo-5β-cholanic acid-3α,7α, 2α-triacetoxy-ethyl ester were: LC-MS (thermospray): 666 $(M+NH_4)^+$, $^{13}C$-NMR: 184.9, 78.6, 77.0, 73.7, 52.0, 51.4, 46.9, 46.4, 44.6, 43.7, 40.7, 40.2, 39.7, 39.2, 34.6, 33.0, 32.6, 32.0, 31.7, 28.3, 27.5, 22.4 and 17.5.

24-carboxy-25-homo-5β-cholanic acid-360 ,7α,12α-triacetoxy-ethyl ester was dissolved in 50 ml ethanol and 10 ml 1N sodium hydroxide was added thereto. The mixture was stirred at room temperature overnight and then acidified with dilute hydrochloric acid. The product precipitated out and was filtered to give 92–95% 24-carboxy-25-homo-5β-cholanic acid-3α,7α,12α-triol as a white solid. Results of analysis of 24-carboxy-25-homo-5β-cholanic acid3α,7α, 12α-triol were: MS (FAB+ve): 467 $(M+H)^+$.

The corresponding homo-derivative, 25-homo-5β-cholanic acid3α,7α,12β-triol, was produced in a similar manner by refluxing overnight.

The diethylmalonate and ethanol can be replaced by dimethylmalonate and methanol, respectively, in this reaction.

The α-carboxy-homo-derivatives of deoxycholic, chenodeoxycholic, ursodeoxycholic and lithocholic acids were prepared in the same manner with similar results.

The reaction scheme of Example 2 is presented below.

Side Chain Lengthening by One Carbon Unit and α—COOH Derivatives

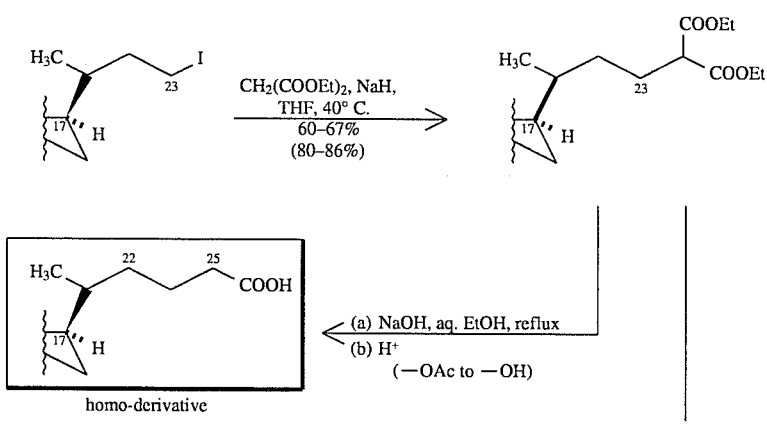

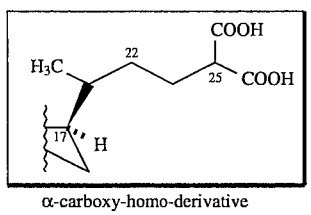

α-carboxy-homo-derivative (a) NaOH, aq. EtOH, room temp.
(b) H⁺
(—OAc to —OH)

EXAMPLE 3

Synthesis of bishomo-derivatives by lengthening side chain by two carbon units (Free Radical Approach)

Methyl or ethyl acrylate (0.108 ml, 1.20 mmol), tris(trimethylsilyl)silane (TTMSS, 0.37 ml, 1.20 mmol), and 10 mol % azobisisobutyronitrile (AIBN) as a free radical initiator was added to a solution of 1.00 mmol iodo-derivative, prepared as described in Example 1, in toluene (20 ml). The mixture was stirred at 70° C. for 2.5 hours. The mixture was purified over silica gel resulting in 61–65% 26-bishomo-5β-cholanic acid-3α,7α,12α-triacetoxy-ethyl ester as a major product and 18–21% 3α,7α,12α-triacetoxy-5δ-cholanic as a minor product. Results of analysis of 26-bishomo-5β-cholanic acid-3α,7α,12α-triacetoxy-ethyl ester were: LC-MS (thermospray): 594 (M+NH$_4$)⁺; $^{13}$C-NMR: 174.2, 170.4, 170.3, 75.5, 74.1, 70.7, 51.4, 47.6, 45.0, 43.3, 40.9, 41.1, 37.7, 35.2, 34.8, 34.6, 34.0, 31.2, 28.8, 27.2, 26.8, 25.6, 25.3, 22.8, 22.5, 21.4, 17.8 and 12.2. Results of analysis of 3α,7α,12β-triacetoxy-5β-cholane were: LC-MS (thermospray): 508 (M+NH$_4$)⁺.

10 ml 1N solution of sodium hydroxide was added to a solution of 26-bishomo-5βD-cholanic acid-3α,7α,12α-triacetoxy-ethyl ester (2.00 mmol) in ethanol (50 ml). The mixture was refluxed overnight. The solvent was evaporated and the residue crystallized from 95% EtOH to yield 95–97% 26-bishomo-5β-cholanic acid-3α,7α,12α-triol as a white solid. Results of analysis of 26 -bishomo-5β-cholanic acid-3α,7α,12α-triol were: LC-MS (thermospray): 440 (M—OH+NH$_4$)⁺.

The bishomo-derivatives of deoxycholic, chenodeoxycholic, ursodeoxycholic and lithocholic adds were prepared in the same manner with similar results.

The reaction scheme of Example 3 is presented below.

Side Chain Lengthening by Two Carbon Units (Free Radical Approach)

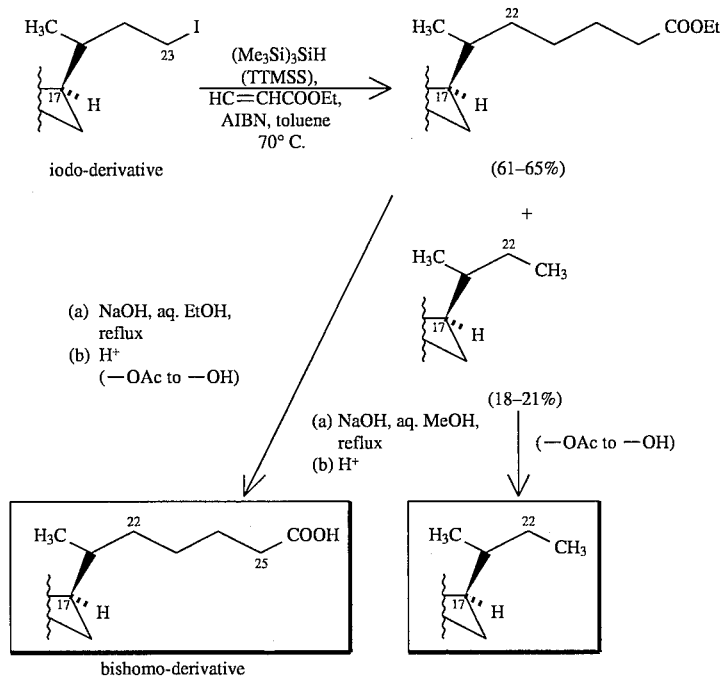

bishomo-derivative

EXAMPLE 4

Synthesis of trishomo-derivatives by lengthening side chain by three carbon units (Free Radical Approach)

An iodo-derivative according to the general formula (III), wherein R$_1$, R$_2$, and R$_3$ each represent a hydroxyl group and R' represents CH$_2$I, was prepared from an acetoxy-derivative of cholic acid (prepared as described in Example 1) by a method reported in the literature (Kihira, K. et al *J Lipid Res* 31: 1323–1326; 1990) starting from chenodeoxycholic acid (3α,7α-dihydroxy bile salt). 5β-cholane-3α,7α,12α-triacetoxy-24-ol was produced as a white solid (77–82%).

Results of analysis of 5β-cholane-3α,7α,12α-triacetoxy-24-ol were: LC-MS (C.I.): 616 (M+)+; $^{13}$C-NMR: 170.4, 170.3, 75.zi, 74.0, 70.6, 63.2, 47.4, 44.9, 43.3, 40.8, 37.6, 34.6, 34.2, 31.5, 31.1, 29.0, 28.8, 27.1, 26.8, 25.4, 22.7, 22.4, 21.4, 21.3, 17.8, and 12.1.

The 5β-cholane-3α,7α,12α-triacetoxy-24-ol was reacted to replace the hydroxyl group with iodine to produce 3α,7α,12α-triacetoxy-24-iodo-5β-cholane. Results of analysis of 3α,7α,12α-triacetoxy-24-iodo-5β-cholane were: LC-MS (thermospray): 648 (M+NH$_4$)+; $^{13}$C-NMR: 170.7, 170.6, 131.7, 130.6, 75.6, 74.3, 70.9, 47.7, 45.3, 43.6, 41.2, 38.0, 36.9, 34.9, 34.6, 31.8, 31.5, 30.3, 29.1, 27.5, 27.1, 25.8, 23.0, 22.8, 22.2, 21.8, 21.7, 18.2, 12.5 and 7.9.

Ethyl acrylate (0.108 ml, 1.20 mmol), TTMSS (0.37 ml, 1.20 mmol), and 10 mol % AIBN as a free radical initiator were added to a solution of 3α,7α,12α-triacetoxy-24-iodo-5β-cholane (1.00 mmol) in toluene (20 ml). The mixture was stirred at 70° C. for 2.5 hours. The mixture was purified with 1:5 ethyl acetate/hexane as the solvent system, followed by 1:3 ethyl acetate to produce 27-trishomo-5β-cholanic acid-3α,7α,12α-triacetoxy-ethyl ester as a white solid (62–65%) and 3α,7α,12α-triacetoxy-23-homocholane as a white solid (23–25%). Results of analysis of 27-trishomo-5β-cholanic acid-3α,7α,12α-triacetoxy-ethyl ester were: LC-MS (thermospray): 608 (M+NH$_4$)+; $^{13}$C-NMR: 174.3, 170.5, 170.4, 75.5, 74.1, 70.8, 51.4, 47.7, 45.0, 43.4, 41.0, 37.8, 35.5, 35.0, 34.7, 34.1, 33.0, 31.3, 29.6, 28.9, 27.3, 26.9, 25.6, 25.0, 22.9, 22.6, 21.6, 21.5 and 17.9. Results of analysis of 3α,7α,12α-triacetoxy-23-homocholane were: LC-MS (thermospray): 522 (M+NH$_4$)+.

10.0 ml 1N sodium hydroxide solution was added to a solution of 27-trishomo-5β-cholanic acid-3α,7α,12α-triacetoxy-ethyl ester (2.00 mmol) in ethanol (50 ml). The mixture was refluxed overnight. The solvent was evaporated and the residue crystallized from 95% EtOH to give 95–86% 27-trishomo-5β-cholanic acid-3α,7α,12α-triol as a white solid. Results of analysis of 27-trishomo-5β-cholanic acid-3α,7α,12α-triol were: LC-MS (thermospray): 454 (M–OH+ NH$_4$)+.

The trishomo-derivatives of deoxycholic, chenodeoxycholic, ursodeoxycholic and lithocholic acids were prepared in the same manner with similar results.

The reaction scheme of Example 4 is presented below.

Side Chain Lengthening by Three Carbon Units (Free Radical Approach)

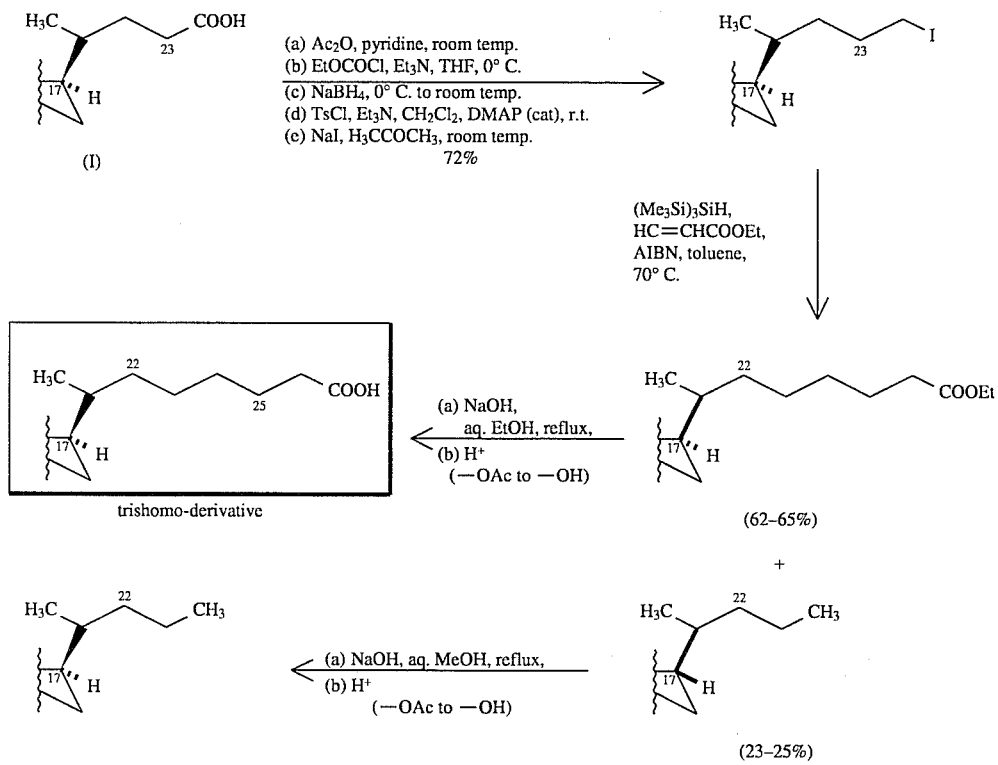

EXAMPLE 5

Synthesis of phosphate derivative by incorporation of phosphate group p-Toluenesulphonic acid (5.05 g, 26.6 mmol) was added to a solution of 5β-cholanic acid-3α,7α,12α-triol (26.6 mmol) in ethanol (250 ml). The mixture was refluxed for 24 hours. The solvent was evaporated and the residue was dissolved in 350 ml CCl$_{14}$. Normal workup followed by purification over silica gel resulted in 92–94% yield of 5β-cholanic acid-3α,7α,12α-triol-ethyl ester.

NaH (2.5 mmol) and benzyl bromide (2.2 mmol) were added to a solution of 5β-cholanic acid-α,7α,12α-triol-ethyl ester (2.00 mmol) in THF (50 ml). The mixture was stirred at 40° C. for 3 hours. The mixture was diluted with 200 ml CH$_2$Cl$_2$ and a saturated solution of NH$_4$Cl (30 ml). The organic layer was collected, washed with water and dried over MgSO$_4$. The solvent was evaporated and the residue purified over silica gel to give a yield of 95–96% 3α-benzyloxy-5β-cholanic acid-7α,12α-diol-ethyl ester A solution of 3α-benzyloxy-5β-cholanic acid-7α,12α,12α-diol-ethyl ester (2.00 mmol) in THF (20 ml) was added dropwise to a solution of lith aluminum hydride (1.0 mmol) in THF (40 ml). The mixture was stirred at room temperature for 3 hours and then diluted with 70 ml EtOAc and a saturated solution of $NH_4Cl$ (20 ml). The organic layer was collected, washed with water and dried over $MgSO_4$. The solvent was evaporated and the residue was purified over silica gel to produce 3α-benzyloxy-5β-cholanic acid-7α,12α-24-triol with a yield of 95–96%.

Sodium hydride (1.0 mmol) was added to a solution of 3α-benzyloxy-5β-cholanic acid-7α,12α-24-triol (1.0 mmol) in THF (30 ml), followed by the addition of 2.00 mmol anhydride of di-O-benzyl phosphate, $(BzO)_2(O)POP(O)(OBz)_2$, in THF (5 ml). The mixture was stirred at room temperature for 3 hours. The reaction was quenched with a saturated solution of $NH_4Cl$ (20 ml) and diluted with 100 ml $CH_2Cl_2$. The organic layer was collected, washed with water and dried over $MgSO_4$. The solvent was evaporated and the residue was purified over silica gel to give a yield of 71–74% of 3α-benzyloxy-24-O-(benzyloxy phosphate)-5β-cholane-7α,12α-diol.

A solution of 3α-benzyloxy-24-O-(benzyloxy phosphate)-5β-cholane-7α,12α-diol in 95% EtOH was hydrogenated under atmospheric pressure in the presence of 10 mol % Pd-C as a catalyst. When the reaction was completed, the catalyst was filtered and the solvent was evaporated to give a yield of 95–96% of 5β-cholane-3α,7α,12α,24-O-(phosphate)-tetrol.

The phosphate derivatives of deoxycholic, chenodeoxycholic, ursodeoxycholic and lithocholic acids were prepared in the same manner with similar results.

The reaction scheme of Example 5 is presented below.

Side Chain: Incorporation of Phosphate Group

A solution of 3α,7α,12α-triacetoxy-5β-cholanic acid-ethyl ester (5 mmol) in dry THF (100 ml) was cooled to –78° C. and lithium diisopropylamide (LDA, 5.98 g, 7.5 mmol) was added thereto. After 15 minutes, a solution of trans-2-(phenylsulfonyl)-3-phenyloxaziridine (Davis reagent, 2.06 g, 6.73 mmol) in THF (10 ml) was added. The mixture was stirred at –60° C. for 3 hours. Normal workup, followed by purification over silica gel gave two diastereomers of 3α,7α,12α-triacetoxy-23-hydroxy-5β-cholanic acid-ethyl ester. The absolute stereochemistry of the diastereomers was not determined.

A solution of one of the diastereomers of 3α,7α,12α-triacetoxy-23-hydroxy-5β-cholanic acid-ethyl ester in aqueous EtOH and 1N NaOH (ratio 3:1) was refluxed overnight. The mixture was hydrolysed with diluted HCl. NaCl separated out and was filtered. The mother liquor was evaporated to dryness to produce a 91–93% yield of 23-hydroxy-5β-cholanic acid-3α,7α,12α-triol. The method was repeated for the other diastereomer of α,7α,12α-triacetoxy-23-hydroxy-5β-cholanic acid-ethyl ester with similar results.

The α-hydroxyl-derivatives of deoxycholic, chenodeoxycholic, ursodeoxycholic and lithocholic acids were prepared in the same manner with similar results.

The reaction scheme of Example 6 is presented below.

Side Chain: Incorporation of —OH Group at an αPosition

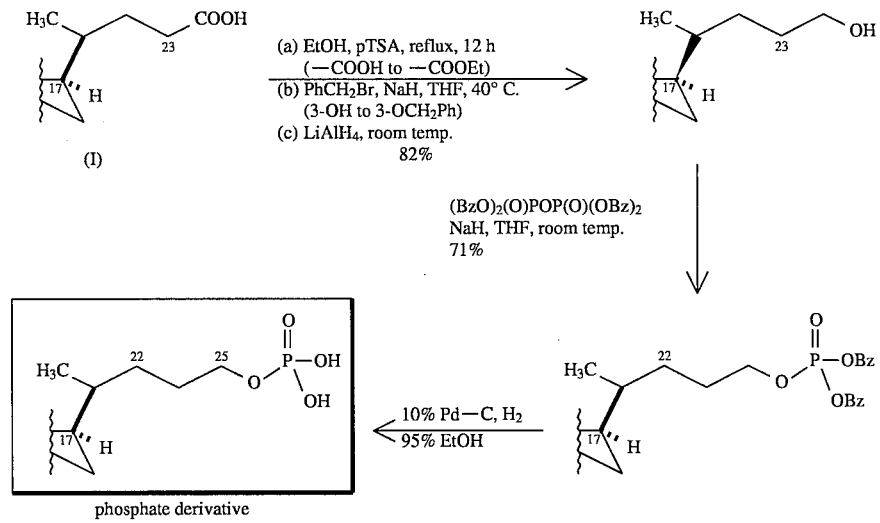

phosphate derivative

EXAMPLE 6

Synthesis of α-hydroxyl derivatives by α-hydroxylation of the side chain

A sample of 3α,7α,12α-triacetoxy-5β-cholanic acid-ethyl ester was prepared in a manner known to those skilled in the art by acetylation of hydroxyl groups and the esterification of the carboxy group.

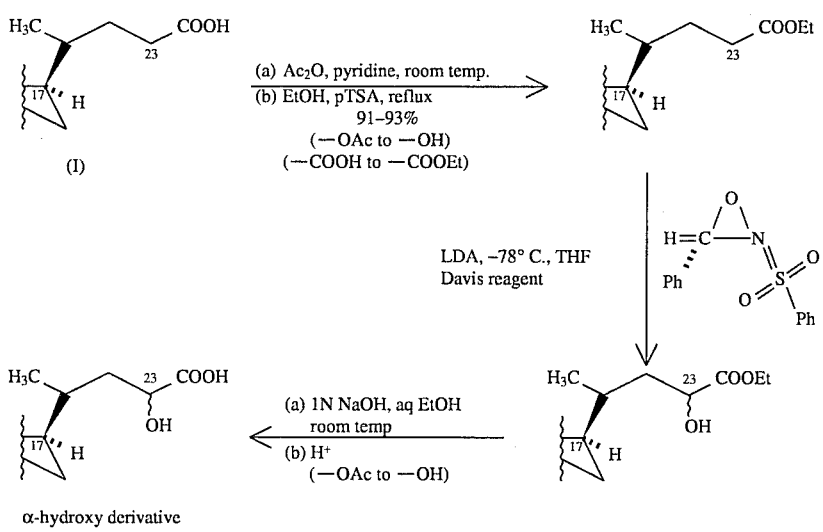

EXAMPLE 7

Synthesis of nitrogen containing side chain derivatives

Potassium carbonate (0.44 g, 3.2 mmol) and piperidine (0.32 ml, 3.20 mmol) were added to a solution of 1.5 mmol iodo-derivative (prepared as described in Example 1) in $CH_3CN$ (75 ml). The mixture was stirred at room temperature for 20 hours. The solution was filtered and the solvent was evaporated to give a yield of 93–95% $3\alpha,7\alpha,12\alpha$-triacetoxy-23-N-piperidino-5βcholane. Results of analysis of $3\alpha,7\alpha,12\alpha$-triacetoxy-23-N-piperidino-5β-cholane were: LC-MS (thermospray): 574 $(M+H)^+$.

10.0 ml 1N sodium hydroxide solution was added to a solution of $3\alpha,7\alpha,12\alpha$-triacetoxy-23-N-piperidino-5β-cholane (2.00 mmol) in methanol (50 ml). The mixture was refluxed overnight. The solvent was evaporated and the residue crystallized from 95% EtOH to give a 95–96% yield of 23-N-piperidino-5β-cholanic acid-$3\alpha,7\alpha,12\alpha$-triol as a white solid.

Potassium carbonate (0.44 g, 3.20 mmol) and piperidine (0.32 ml, 3.20 mmol) were added to a solution of 1.60 mmol iodo-derivative (prepared as described in Example 4) in $CH_3CN$ (75 ml). The mixture was stirred at room temperature for 20 hours. The solution was filtered and the solvent was evaporated yielding 92% $3\alpha,7\alpha,12\alpha$-triacetoxy-23-N-piperidino-homo-5β-cholane. Results of analysis of $3\alpha,7\alpha,12\alpha$-triacetoxy-23-N-piperidino-homo-5β-cholane were: LC-MS (thermospray): 588 $(M+H)^+$.

10.0 ml 1N sodium hydroxide solution was added to a solution of $\alpha,7\alpha,12\alpha$-triacetoxy-23-N-piperidino-homo-5β-cholane (2.00 mmol) in methanol (50 ml). The mixture was refluxed overnight. The solvent was evaporated and the residue crystallized from 95% EtOH to give 24-N-piperidino-5β-cholanic acid-$3\alpha,7\alpha,12\alpha$-triol as a white solid with a yield of 95 . 96%.

The analogous side chain derivatives of deoxycholic, chenodeoxycholic, ursodeoxycholic and lithocholic acids were prepared in the same manner with similar results.

The reaction scheme of Example 7 is presented below.

Nitrogen Containing Side Chain

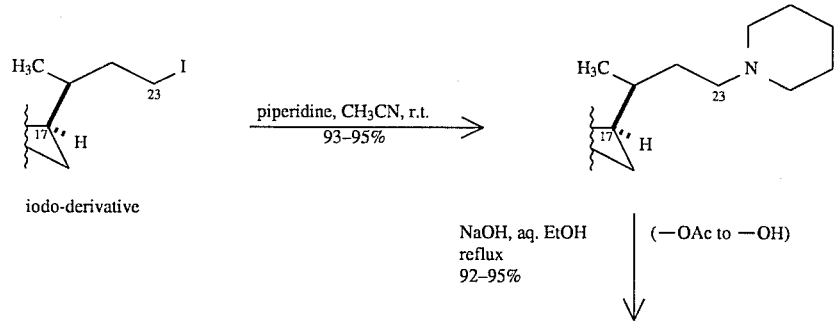

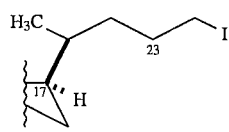

iodo-derivative piperidine, CH₃CN, r.t.
93–95%

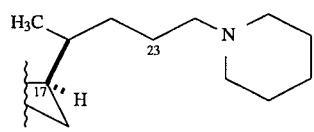

NaOH, aq. EtOH
reflux
92–95%
(—OAc to —OH)

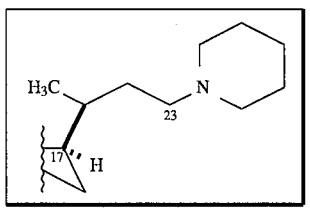

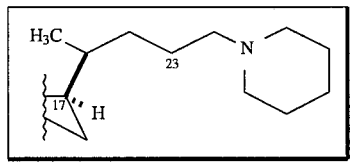

EXAMPLE 8

Synthesis of L-aspartate, L-glutamate, L-lysine, R-phenylglycine, 12-aminododecanoic acid and 4-aminohippuric acid conjugate derivatives To a solution of 5β-cholanic acid-3α,7α,12α-triol (10.0 mmol) in THF (50 ml) under nitrogen was added dicyclohexylcarbodiimide (DCC, 10.0 mmol), the hydrochloride of N-CBz (in the side chain) ethyl ester derivative of L-lysine (10.0 mmol), triethyl amine (10.0 mmol) and 10 mol % DMAP as a catalyst. The mixture was stirred at room temperature for 16–24 hours. The solution was filtered and the solvent was evaporated. The residue was collected and was purified over silica gel to give N-carbobenzyloxy-lysine ethyl ester conjugate as a white solid (91–95% yield). Results of analysis of N-carbobenzyloxy-lysine ethyl ester conjugate were: MS (FAB +ve): 685 (M+H)⁺.

1N NaOH (15 ml) was added to a solution of N-carbobenzyloxylysine conjugate (10.00 mmol) in ethanol (40 ml). The mixture was stirred at room temperature for 10–15 hours and acidified with diluted HCl. NaCl separated from the solution and was filtered. The mother liquor was evaporated to dryness yielding 90–95% L-lysine conjugate derivative of cholic acid as a white solid.

The experiment was repeated with the hydrochloride of diethyl ester derivative of L-aspartic acid, hydrochloride of diester derivative of L-glutamic acid, hydrochloride of ethyl ester derivative of R-phenylglycine, the hydrochloride of ethyl ester derivative of 12-aminododecanoic acid and the hydrochloride of ethyl ester derivative of 4-aminohippuric acid. Similar results were obtained for the corresponding conjugate derivatives of cholic acid.

The L-aspartate, L-glutamate, L-lysine, R-phenylglycine, 12-aminododecanoic acid and 4-aminohippuric acid conjugate derivatives of deoxycholic, chenodeoxycholic, ursodeoxycholic and lithocholic acids were prepared in the same manner with similar results.

The reaction scheme of Example 8 is presented below.

L-Aspartic acid, L-Glutamic and L-Lysine, R-Phenylglycine, 12-Aminododecanoic acid and 4-Aminohippuric acid Conjugate Derivatives

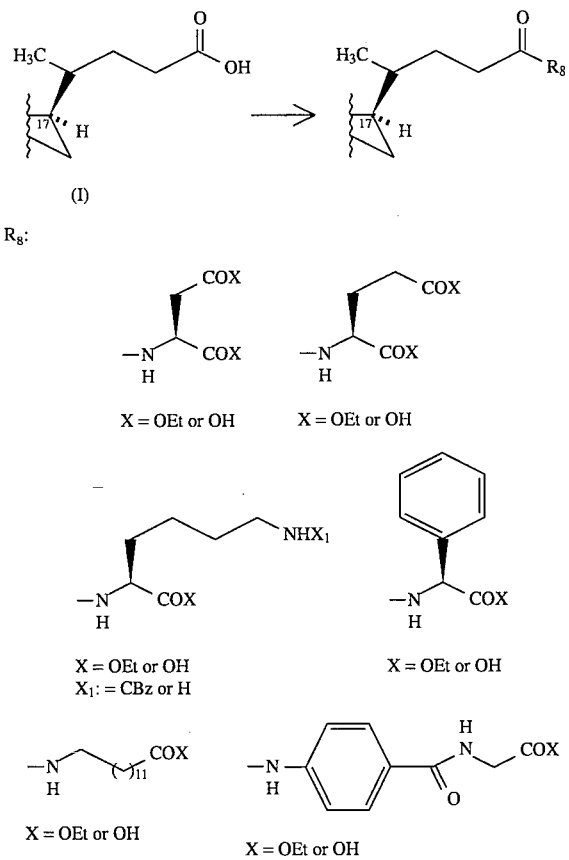

We claim:

1. A bile acid according to the general formula (I)

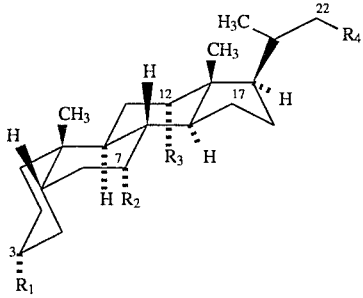 (I)

wherein $R_1$ represents a hydroxyl group, $R_2$ and $R_3$ both represent a hydroxyl group, or $R_2$ represents a hydroxyl group or a β-hydroxyl group and $R_3$ represents hydrogen, and $R_4$ represents —$(CH_2)_n R_5$ wherein n is from 1 to 6 and $R_5$ represents:

(i) —O—PO(OH)$_2$, or —CH(OH)COOH, or (ii) —CO—$R_8$ or —CO—NHC$_6$H$_4$—CO—NHCH$_2$COOH, wherein $R_8$ represents an amino acid moiety.

2. A bile acid according to claim 1, wherein $R_5$ represents O—PO(OH)$_2$.

3. A bile acid according to claim 1, wherein $R_5$ represents CH(OH)COOH.

4. A bile acid according to claim 1, wherein $R_5$ represents COR$_8$ and represents L-aspartic acid or L-glutamic acid.

5. A bile acid according to claim 1, wherein $R_5$ represents COR$_8$ and $R_8$ represents L-lysine.

6. A bile acid according to claim 1, wherein $R_5$ represents COR$_8$ $R_8$ represents R-phenylglycine or R-naphthylglycine.

7. A bile acid according to claim 1, wherein $R_5$ represents COR$_8$ and $R_8$ represents NH(CH$_2$)$_m$COOH wherein m is from 3 to 12.

8. A bile acid according to claim 1, wherein $R_5$ represents —CONHC$_6$H$_4$CONHCOCH$_2$COOH.

* * * * *

UNITED STATES PATENT AND TRADEMARK OFFICE
CERTIFICATE OF CORRECTION

PATENT NO. : 5,541,348

DATED : July 30, 1996

INVENTOR(S) : Prabhat Arya and Graham W. Burton

It is certified that error appears in the above-indentified patent and that said Letters Patent is hereby corrected as shown below:

Title page, Item [75],

The first inventors last name "Ayra" should be --Arya-- as requested in our letter dated 16 April 1996.

IN THE DISCLOSURE:

Col. 11, l. 21    "a-homo-carboxy" should be --α-homo-carboxy--

Col 16, l. 40-44    formula

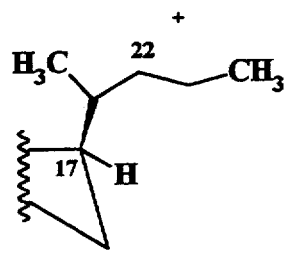

UNITED STATES PATENT AND TRADEMARK OFFICE
CERTIFICATE OF CORRECTION

PATENT NO. : 5,541,348

DATED : July 30, 1996

INVENTOR(S) : Prabhat Arya and Graham W. Burton

It is certified that error appears in the above-indentified patent and that said Letters Patent is hereby corrected as shown below:

should read:

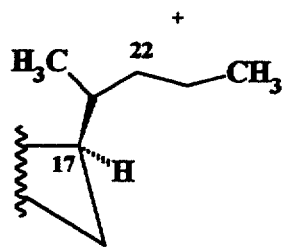

UNITED STATES PATENT AND TRADEMARK OFFICE
CERTIFICATE OF CORRECTION

PATENT NO. : 5,541,348

DATED : July 30, 1996

INVENTOR(S) : Prabhat Arya and Graham W. Burton

It is certified that error appears in the above-indentified patent and that said Letters Patent is hereby corrected as shown below:

Col 20, 10-15, beside the "Davis reagent", formula

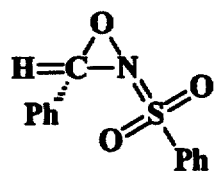

should read —    —

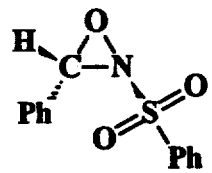

Signed and Sealed this

Twenty-fifth Day of February, 1997

Attest:

BRUCE LEHMAN

Attesting Officer

Commissioner of Patents and Trademarks